US012773470B2

(12) United States Patent
Ghodbane et al.

(10) Patent No.: US 12,773,470 B2
(45) Date of Patent: Oct. 27, 2026

(54) PLUG FOR LUNG TISSUE TRACT SEALING

(71) Applicant: Ethicon, Inc., Raritan, NJ (US)

(72) Inventors: Salim Ghodbane, Piscataway, NJ (US); Sridevi Dhanaraj, Raritan, NJ (US); Ashley DeAnglis, Skillman, NJ (US); Guanghui Zhang, Belle Mead, NJ (US)

(73) Assignee: Ethicon, Inc., Raritan, NJ (US)

( * ) Notice: Subject to any disclaimer, the term of this patent is extended or adjusted under 35 U.S.C. 154(b) by 923 days.

(21) Appl. No.: 18/048,508

(22) Filed: Oct. 21, 2022

(65) Prior Publication Data

US 2023/0132953 A1 May 4, 2023

Related U.S. Application Data

(60) Provisional application No. 63/275,487, filed on Nov. 4, 2021.

(51) Int. Cl.
*A61L 24/00* (2006.01)
*A61L 24/04* (2006.01)
*F41A 19/24* (2006.01)

(52) U.S. Cl.
CPC ....... *A61L 24/0036* (2013.01); *A61L 24/0015* (2013.01); *A61L 24/043* (2013.01); *F41A 19/24* (2013.01); *A61L 2300/252* (2013.01); *A61L 2300/418* (2013.01); *A61L 2400/04* (2013.01); *A61L 2430/36* (2013.01)

(58) Field of Classification Search
CPC .................................................. A61L 24/0036
See application file for complete search history.

(56) References Cited

U.S. PATENT DOCUMENTS

| | | | | |
|---|---|---|---|---|
| 8,292,918 | B2 | 10/2012 | Hill et al. | |
| 2008/0187591 | A1* | 8/2008 | Rhee | A61K 38/363 424/94.64 |
| 2009/0286886 | A1* | 11/2009 | Fisher | A61L 24/0042 523/105 |
| 2011/0021964 | A1* | 1/2011 | Larsen | A61P 17/02 602/47 |
| 2012/0101519 | A1* | 4/2012 | Hill | A61B 17/0057 606/213 |
| 2021/0213157 | A1 | 7/2021 | Deanglis et al. | |

FOREIGN PATENT DOCUMENTS

WO WO-2010064251 A1 * 6/2010 ............ A61K 47/60

OTHER PUBLICATIONS

Yousem et al., "Pulmonary Pathologic Alterations Associated with Biopsy Inserted Hydrogel Plugs", Human Pathology, vol. 89, Apr. 20, 2019, pp. 4-43.
International Search Report and Written Opinion for PCT Application No. PCT/IB2022/060146, mailed on Jan. 26, 2023, 13 pages.

* cited by examiner

*Primary Examiner* — Erin Mcgrath
(74) *Attorney, Agent, or Firm* — David R. Crichton; Leo B. Kriksunov

(57) ABSTRACT

The present invention provides a tissue sealing plug comprising a substrate comprising foamed gelatin impregnated with polyethylene glycol that is liquid at room temperature, wherein the weight ratio of polyethylene glycol to foamed gelatin in the substrate is about 4:1 to about 6.8:1 and the substrate is substantially free of air, along with methods of using the plug for closing tissue punctures in the lung.

8 Claims, 3 Drawing Sheets

PLUG FOR LUNG TISSUE TRACT SEALING

FIELD OF THE INVENTION

The present invention provides a tissue sealing plug comprising a compressed substrate comprising foamed gelatin having an interconnected pore structure impregnated with liquid polyethylene glycol having a viscosity of about 30 to about 260 cP at room temperature (about 20-25 C) and substantially free of non-aqueous solvents, along with methods of using the plug for closing punctures in the lung such as those created by lung biopsies.

BACKGROUND OF THE INVENTION

Image-guided percutaneous transthoracic needle biopsy ("PTNB") is an established procedure for patients with suspected pathologic processes, such as bronchogenic carcinoma. The goal of the procedure is to obtain tissue for cytologic or histologic examination. The procedure is typically performed with image guidance by a radiologist. Imaging modalities utilized include fluoroscopy, computed tomography (CT), and ultrasonography.

PTNB is classified according to the type of needle. Fine needle aspiration biopsy is performed to provide cytological specimens and larger diameter cutting needles produce histological specimens. Historically, cutting needles have been associated with a relatively high incidence of complications, but with the introduction of automated cutting needles comparable rates between fine needle aspiration and cutting needles have been demonstrated.

During PTNB, an aspiration (18-22 gauge) or cutting needle (14-20 gauge) is placed under image guidance for sample recovery. A coaxial technique may be used to allow for multiple passes within the lung tract and to reduce the number of pleural punctures. In this technique, a thin-walled introducer needle (13-19 gauge) is first inserted, localized to the lesion, and subsequently the aspiration or cutting needle is inserted.

Although the procedure is considered safe and effective, the incidence of pneumothorax is still significant, ranging from 12 to 61%, with 2 to 15% requiring a chest drain. The risk of pneumothorax increases significantly if the lesion is not adjacent to the pleura. Most complications occur immediately or within the first hour following the biopsy. Therefore, following the procedure, the patient is placed in a puncture-site-down position and remains under supervision for at least one hour.

As an alternative to PTNB, transbronchial needle aspiration ("TBNA") is a minimally invasive technique allowing for the sampling of mediastinal nodes. When integrated with endobronchial ultrasonography ("EBUS"), accurate definition of mediastinal structures is possible. Modern devices integrate an ultrasonic bronchoscope into the needle allowing for real time visualization of the area of interest. The diagnostic yield of EBUS-TBNA in lung cancer screening has been reported to have a sensitivity as high as 95.7%. As a result, EBUS-TBNA is becoming widely adopted as the standard of care for sampling mediastinal lymph nodes.

EBUS-TBNA devices include an ultrasound linear processing array and a retractable needle. EBUS-TBNA was originally performed with a dedicated 22-gauge aspiration needle; however, larger 21-gauge needles were introduced more recently. EBUS-TBNA are carried out in the proximal lumen of level 9 bronchi, as they are restricted by the outer diameter of the bronchoscope (6.9 mm).

Although complications are very low in EBUS-TBNA, incidence of pneumothorax is still significant. The rate of pneumothorax has been estimated to be from 0.53% to 16.7% following EBUS-TBNA. Moreover, PTNB and EBUS-TBNA procedures result in relatively large, cylindrical lesions along the order of 28 mm in diameter and 5 cm in length.

Patients in which enlarging pneumothoraxes are observed must be treated with the placement of a chest tube. However, there is no universally accepted approach to reduce pneumothorax rate. Multiple solutions have been employed, including the rapid roll over and deep expiration and breath-hold technique, but these techniques have only shown mild/moderate effects, with a risk reduction of 0.1-15.7%.

Others have investigated the instillation of various sealant materials into the lesion, including autologous blood clot, fibrin glue, and gelatinous foam, but none have achieved widespread use in daily practice. These methods have also suffered from variable results, possibly a result of operator-dependence and variations in practice. Autologous blood clot has demonstrated moderate efficacy but suffers from long preparation times in the operating room. Although fibrin glue and gelatin techniques have demonstrated some promising results in published data, they have not been studied extensively.

More recently, a synthetic polyethylene glycol plug has been commercialized as part of the BIOSENTRY™ Tract Sealant System (AngioDynamics, Inc.). In a randomized, multicenter clinical trial, the BIOSENTRY system resulted in the absence of pneumothorax in 85% of patients which was statistically greater than the control group (69%). However, as reported by Yousem, S. A., et al., *Pulmonary pathologic alterations associated with biopsy inserted hydrogel plugs*. Hum Pathol, 2019. 89: p. 40-43, the solid nature of the BIOSENTRY plug induces only a foreign body giant cell reaction and an encapsulation of the hydrogel by 21 days. Accordingly, a more porous plug would lead to a reduced foreign body reaction and more rapid healing.

U.S. Pat. No. 8,292,918 relates to a composite plug for arteriotomy closure that comprises an elongate substrate member and one or more continuous or discontinuous layers disposed at least in part about the substrate member. The plug comprises a distal end, a proximal end, and a lumen connecting the distal and proximal ends, the lumen sized to receive a suture. The substrate member may comprise a foamed gelatin and the layers may comprise a hydrogel or hemostatic material. The hydrogel, if present, may comprise polyethylene glycol in the molecular weight range of about 600 to 6000.

SURGIFOAM® Absorbable Gelatin Sponges, commercially available from Ethicon, Inc., Somerville, NJ, are cross-linked, gelatin-based hemostats in dry, solid, sponge form. SURGIFOAM Absorbable Gelatin Sponges are sterile, porcine, absorbable gelatin sponges capable of liquefying within 2 to 5 days when applied to bleeding mucosal regions and are completely absorbed within 4 to 6 weeks. SURGIFOAM sponges are available in two shapes, cube or flat. Although gelatin is known to absorb 40 times its weight in blood and swell to up to 200% of its initial volume in vivo, this swelling is relatively slow and results in a low swelling pressure. Accordingly, SURGIFOAM® labeling advices, "[w]hen placed into cavities or closed tissue spaces, minimal preliminary compression is advised, and care should be exercised to avoid overpacking (the sponge expands upon absorption of liquid). SURGIFOAM® Sponge may swell to its original size on absorbing fluids, creating the potential for nerve damage."

SUMMARY OF THE INVENTION

The present invention provides a tissue sealing plug comprising a compressed substrate comprising foamed gelatin having an interconnected pore structure impregnated with liquid polyethylene glycol having a viscosity of about 30 to about 260 cP at room temperature and substantially free of non-aqueous solvents, wherein the weight ratio of polyethylene glycol to foamed gelatin in the substrate is about 4:1 to about 6.8:1 and the plug has a porosity of less than 30%.

The present invention also provides a method of closing a lung tract, comprising in sequence: (i) inserting into the lung tract a tissue sealing plug comprising a compressed substrate comprising foamed gelatin having an interconnected pore structure impregnated with liquid polyethylene glycol having a viscosity of about 30 to about 260 cP at room temperature and substantially free of non-aqueous solvents, wherein the weight ratio of polyethylene glycol to foamed gelatin in the substrate is about 4:1 to about 6.8:1 and the plug has a porosity of less than 30%; and (ii) injecting an aqueous solution into the compressed substrate of the tissue sealing plug.

Applicants have now discovered that an improved tissue sealing plug having particular benefits for sealing lung tracts resulting from, for example from PTNB and EBUS-TBNA, may be prepared by impregnating a substrate comprising foamed gelatin with liquid polyethylene glycol having a viscosity of about 30 to about 260 cP at room temperature and substantially free of non-aqueous solvents, wherein the weight ratio of polyethylene glycol to foamed gelatin in the substrate is about 4:1 to about 6.8:1 and the plug has a porosity of less than 30%. Contrary to the conventional use of foamed gelatins, the plug may be compressed and rolled into a plug due to the impregnation of PEG liquid in the foamed gelatin. When impregnated, the plug is conformable and flexible even without the introduction of water. If the plug is maintained in a dry environment, the PEG acts as a binder to hold its shape and provides rigidity. When inserted into a lung tract, the plug advantageously, when injected with an aqueous component, hydrates and expands to the shape of the tract, immediately forming a mechanical seal. Use of the plug is highly effective to achieve pneumostasis and hemostasis control even in larger tracts resulting from PTNB or EBUS-TBNA procedures.

DETAILED DESCRIPTION OF THE INVENTION

Figure 1:
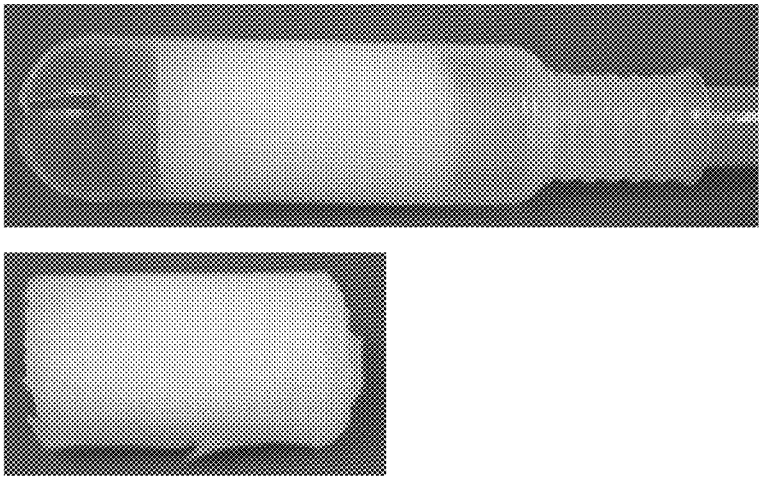
FIG. 1 is a photograph of the prototype tissue sealing plug of Example 2 prior to use.

As used herein, "foam" or "foamed" means a solid, porous material having pores that are internal or below an exterior facing surface with at least a portion of such pores being open to the surface of the material.

As used herein, "impregnated with" means filled with or containing such that the polyethylene glycol is both absorbed and adsorbed into the substrate. That is, the polyethylene glycol substantially fills the available pores of the foamed gelatin, for example as a result of compression induced capillary action, followed by absorption of the PEG into the bulk phase of the gelatin causing the gelatin fibers to swell. The PEG is additionally be adsorbed into the substrate itself.

As used herein, "substantially free of non-aqueous solvent" means containing less than 1% weight percent, for example less than 0.1% weight percent.

As used herein, "substantially free of air" means containing less than 30% volume percent, for example less than 10% volume percent.

As used herein, "biocompatible" means compatible with living tissue or a living system by not being toxic, injurious, or physiologically reactive therewith and not causing immunological rejection thereby.

As used herein, "biologically absorbable" or "resorbable" means capable of degradation in the body to smaller molecules having a size that allows them to be transported into the blood stream. Such degradation and transportation gradually remove the material referred to from the site of application. For example, gelatin can be degraded by proteolytic tissue enzymes to absorbable smaller molecules, whereby the gelatin, when applied to tissue, typically is absorbed within about 4-6 weeks, and when applied to bleeding surfaces or mucous membranes, typically liquefies within 3-5 days.

As used herein, "hemostasis" means the process by which bleeding diminishes or stops. During hemostasis three steps occur in a rapid sequence. Vascular spasm is the first response as the blood vessels constrict to reduce blood loss. In the second step, platelet plug formation, platelets stick together to form a temporary seal to cover the break in the vessel wall. The third and last step is called coagulation or blood clotting. Coagulation reinforces the platelet plug with fibrin threads that act as a "molecular glue." Accordingly, a hemostatic material or compound is capable of stimulating hemostasis.

Unless otherwise indicated, percentages and amounts refer to percentages or amounts by weight, and ratios are weight ratios. Unless stated otherwise, all ranges are inclusive of the endpoints, e.g., "from 4 to 9" includes the endpoints 4 and 9.

The Foam Substrate

The foam substrate is composed primarily of a gelatin. Gelatin, which is a denatured form of the protein collagen, has been used in a variety of wound dressings. Since gelatin gels have a relatively low melting point, they are not very stable at body temperature. Therefore, it is imperative to stabilize these gels by establishing cross-links between the protein chains. In practice, this is usually obtained by treating the gelatin with glutaraldehyde or formaldehyde. Thus cross-linked gelatin may be fabricated into dry sponges which are useful for inducing hemostasis in bleeding wounds or ground into particulate form.

The term "gel" is used herein to denote a swollen, hydrated polymer network which is essentially continuous throughout its volume. A protein gel is composed of an essentially continuous network of linked protein molecules and a liquid (typically aqueous) solvent, which fills the space within the protein matrix. The protein matrix exerts a strong viscous drag on the solvent molecules, preventing them from flowing freely. The component molecules making up the gel network may be linked by ionic, hydrophobic, metallic or covalent bonds. The covalent bond is the most thermally stable of these bonds.

A particularly preferred substrate is made from the SURGIFOAM gelatin sponge, which has open cell pore structure, not a closed cell foam. Typical pore cell diameter is 95-450 micrometers. The SURGIFOAM gelatin sponge meets the requirements of Absorbable Gelatin Sponge as defined by the United States Pharmacopeia, including the water absorption requirement of absorbing not less than 35 times of its weight of water.

The tissue sealing plug comprises a substrate of foamed gelatin. The substrate may comprise a foamed gelatin. The substrate may consist essentially of a foamed gelatin. The substrate may consist of a foamed gelatin.

The gelatin typically originates from a porcine source, but may originate from other animal sources, such as from bovine or fish sources. The gelatin may be synthetically made, i.e., by recombinant means. The gelatin may be cross-linked. Any suitable cross-linking methods known to a person skilled on the art may be used including both chemical and physical cross-linking methods.

The gelatin has an interconnected pore structure. As used herein, "interconnected pore structure" means having an open cell pore structure (rather than a closed pore structure). The cell diameter of the pores may be about 95 to about 450 micrometers.

The substrate may have a variety of shapes. The substrate may be cylindrical or spherical. A cylindrical substrate may be made, for example, by rolling one or more rectangular pieces into a cylinder. A cylindrical substrate may have a longitudinally tapered width, that is, its diameter decreases along its length from one end to the other.

A suitable gelatin sponge for use in or as the substrate is SURGIFOAM® Absorbable Gelatin Sponge commercially available from Ethicon, Inc. Other commercially available absorbable gelatin materials useable in or as the substrate include GELFOAM (Pfizer), CURASPON (Cura Medical), GELITASPON (Gelita Medical), and GELASPON (KDM). Other gelatin foams meeting the definition of Absorbable Gelatin Sponge set forth in the United States Pharmacopeia, including the water absorption requirement of absorbing not less than 35 times of its weight of water, may be used.

The substrate may optionally include surface features. For example, the substrate may comprise lines, ribs, barbs, grooves, notches, slits, channels, spikes, steps and combinations thereof. The features may be imparted to the substrate before or after loading with PEG. The features may be added by scoring, cutting, or other mechanical means, or imparted to the substrate during molding (described below) via features on the inside surface of the mold. The gelatin substrate itself, prior to impregnating with the PEG, may contain up to about 10% by weight water.

Polyethylene Glycol

The preferred gelatin modifier that impregnates the substrate is composed principally of a polyethylene glycol having a molecular weight (whether as a blend or pure PEG formulation) that is liquid having a viscosity of about 30 to about 260 cP at room temperature and is substantially free of non-aqueous solvents. Applicants have discovered that loading of the substrate with liquid PEG having a certain viscosity, in a certain amount, and without solvents results in a plug of optimum size and swelling properties. PEG acts as a plasticizer for the substrate and provides flexibility to the substrate. Moreover, since PEG is substantially non-aqueous, the stability of the foamed gelatin is not affected, yet the PEG acts as a wetting agent that can further increase the rate of hydration of foamed gelatin.

The PEG modifier component is substantially free of non-aqueous solvents, such as ethanol, methanol, or acetone. This is advantageous because it enables large diameter plugs (i.e., 20 mm) to be made. Additionally, removal of non-aqueous solvents must be done by evaporation or other means. Removal of large amounts of solvent from a large plug would be time consuming and likely incomplete. Hence, the PEG modifier component should be substantially anhydrous. That is, the PEG modifier component may contain up to about 10% by weight water. Preferably, the PEG modifier component contains no water.

The PEG modifier component is liquid at room temperature and at normal atmospheric pressure (1 atm). The PEG modifier component will generally consist of one or more PEG-based materials have a molecular weight of about 100 to about 600 Da. The PEG modifier component may one or more PEG-based materials having a molecular weight of about 300 to 450 Da.

The amount of liquid PEG modifier that is introduced into the substrate is such that the weight ratio of liquid PEG to the foamed gelatin is about 4:1 to about 6.8:1. That is, the PEG loading is about 4:1 to about 6.8:1 by weight on the weight of the foamed gelatin in the substrate. As the PEG occupies the pores of the cylinder, as the weight ratio of the PEG is increased, the porosity of the plug decreases. As such, a PEG loading ratio of 4:1 by weight results in a plug with a porosity of about 30%. A PEG loading ratio of 5:1 by weight results in a plug with a porosity of about 20%. A PEG loading ratio of 6:1 by weight results in a plug with a porosity of about 10%. A PEG loading ratio of 6.8:1 by weight results in a plug with a porosity of about 0%.

Other Agents

The tissue sealing plug may be administered at the same time as, or itself comprise, one or more other biocompatible agents, such as those capable of stimulating hemostasis, wound healing, or tissue healing.

Examples of other agents include bioactive and non-bioactive agents including without limitation contrast agents such as iohexol, anti-infectives, such as antibiotics and antiviral agents; analgesics and analgesic combinations; anti-helmintics; antiarthritics; anticonvulsants; antidepressants; antihistamines; anti-inflammatory agents; antimigraine preparations; antineoplastics; anti-parkinsonism drugs; antipsychotics; antipyretics, antispasmodics; anticholinergics; sympathomimetics; xanthine derivatives; cardiovascular preparations including calcium channel blockers and beta-blockers such as pindolol and antiarrhythmics; antihypertensives; diuretics; vasodilators, including general coronary, peripheral and cerebral; central nervous system stimulants; hormones, such as estradiol and other steroids, including corticosteroids; immunosuppressives; muscle relaxants; parasympatholytics; psychostimulants; naturally derived or genetically engineered proteins, polysaccharides, glycoproteins, or lipoproteins; oligonucleotides, antibodies, antigens, cholinergics, chemotherapeutic s, radioactive agents, radiopacity agents, osteoinductive agents, cystostatics heparin neutralizers, procoagulants and hemostatic agents, such as prothrombin, thrombin, fibrinogen, fibrin, fibronectin, heparinase, Factor X/Xa, Factor VII/VIIa, Factor VIII/VIIIa, Factor IX/IXa, Factor XI/XIa, Factor XII/XIIa, Factor XIII/XIIIa, tissue factor, batroxobin, ancrod, ecarin, von Willebrand Factor, platelet surface glycoproteins, vasopressin, vasopressin analogs, epinephrine, selectin, procoagulant venom, plasminogen activator inhibitor, platelet activating agents and synthetic peptides having hemostatic activity, and antifibrinolytic agents, such as aprotinin, epsilon aminocaproic acid and tranexamic acid.

Method of Preparing the Plug

A substrate of desired shape and size is first prepared from a selected foamed gelatin. It is then contacted with the PEG modifier component by dipping, spraying, coating, or other means, such that the PEG modifier component is impregnated into the substrate. The PEG-loaded gelatin foam may additionally be compressed manually to substantially remove substantially all the air from the plug.

Alternatively, in order to control the degree of swelling of the plug further, the substrate may be compressed prior to, during or after loading of the PEG modifier component. Conventional foamed gelatins are rigid and brittle, and difficult to roll or compress and susceptible to tearing and fracture. However, according to the invention, a substrate comprising foamed gelatin that has been impregnated with the liquid PEG modifier component may be loaded into a mold or other vessel having a reduced volume, i.e., about 3 to about 5 times smaller than the starting size (volume) of the substrate. As stated infra, the mold may include features on its inside surface to impart structural features to the plug during its preparation.

The resulting plug comprises PEG modifier component that has been absorbed and adsorbed into the substrate such that the plug has a porosity of less than 30%. The plug may have a porosity of less than 10%.

The "porosity" of the plug is determined by the following method based on the mass of the gelatin substrate and residual PEG measured in the plug. The volume of the gelatin substrate and the PEG are first calculated based on their densities. The volume of the final plug is determined. The difference between these volumes is used to calculate the porosity of the plug.

The substrate hydrated with PEG modifier component may be optionally loaded into an applicator. Applicators, including needles, stylets, and the like are known in the art. For example, an 18-gauge needle or coaxial needle may be used as the applicator.

The PEG-loaded gelatin foam substrate is dried for 8-12 hours under nitrogen or other inert atmosphere at room temperature.

For example, a tissue sealing plug according to the invention may be made using SURGIFOAM Absorbable Gelatin Sponges and a liquid PEG modifier component having a molecular weight of 300 Da. A substrate is first made using two strips of SURGIFOAM Absorbable Gelatin Sponges (each 3 cm×12.5 cm×1 cm). The two strips are rolled together to produce a substrate having an initial volume of about initial volume 75 $cm^3$. This substrate is compressed using a mold into a cylindrical geometry with a diameter of about 19 mm, a length of about 3 cm, and a volume of about 8.5 $cm^3$, about a 4.35-fold decrease in volume relative to its initial size. The PEG modifier component is injected into the mold to load about 4:1 to about 6.8:1 by weight of the liquid PEG on the weight of the substrate. This loading ratio saturates the gelatin foam material, causing the gelatin fibers and films to swell, decreasing the surface energy of the gelatin but imparting flexibility to it. The PEG loaded substrate is dried of any residual moisture in a nitrogen environment at room temperature overnight. The resulting plug is cohesive and somewhat stiff.

The plug may have a diameter of about 1 mm to about 28 mm depending on the end use. The plug may have a diameter of about 10 mm to about 20 mm. The diameter of the plug may be about 1 mm for needle biopsies. The diameter of the plug may be about 28 mm for lung tract sealing.

In one embodiment, the plug, once rolled in a mold, is forced into a needle, for example an 18-gauge needle. The plug is dried of any residual moisture in a nitrogen environment at room temperature overnight. The resulting plug has a diameter of 0.41-1.8 mm.

The PEG modifier component acts as a neat solvent in this system to introduce flexibility to the otherwise rigid gelatin sponge. The gelatin sponge is stable when exposed to PEG modifier component unlike an aqueous solvent.

Use of the Plug

When such a tissue sealing plug according to the invention is placed into an enclosed geometry, such as a lung tract, the plug expands to fill the geometry. Once implanted, the plug continues to hydrate until osmotic pressure of the plug is balanced by the pressure imposed on the plug by the surrounding tissue.

The plug may be implanted into a lung tissue tract with the aid of an aqueous medium. The aqueous medium is injected into the plug once the plug is placed into the tract. For example, the aqueous medium may be injected into the center of the implanted plug using a needle. As the aqueous medium is injected, the tip of the needle may be withdrawn along the length of the plug to ensure uniform hydration of the plug with the aqueous medium.

The injection of the aqueous medium into the substrate of the plug results in hydrodynamic pressure on the plug to force rapid hydration. Once initially wet, the gelatin substrate's ability to swell further increases the rate of hydration. When hydrated, for example, with Phosphate Buffered Saline (PBS), the plug can potentially return to its initial volume prior to loading of the PEG and expand further due to swelling of the plug, for instance on the order of a 120%, 150%, 180%, or 200% increase in volume. A fully hydrated plug according to the invention can swell to about 8.7 times its initial volume prior to loading with PEG (unconstrained).

The aqueous medium may comprise, for example, water, saline or a buffered aqueous medium. The aqueous medium is preferably sterile. The aqueous medium may be a saline solution. The aqueous medium may be a calcium chloride solution. The aqueous medium may be water. The aqueous medium may be a buffered aqueous medium. A variety of suitable buffering agents are known in the art and may be used, such as Sodium citrate; Citric acid, Sodium citrate; Acetic acid, Sodium acetate; $K_2HPO_4$, $KH_2PO_4$; $Na_2HPO_4$, $NaH_2PO_4$; CHES; Borax, Sodium hydroxide; TAPS; Bicine; Tris; Tricine; TAPSO; HEPES; TES; MOPS; PIPES; Cacodylate; SSC; MES, or others. For example, the aqueous medium may be Phosphate Buffered Saline (PBS).

The plug may be applied in combination with a biosynthetic, synthetic, or biological liquid sealant to assist with pneumostasis and hemostasis control. For example, the liquid sealant can include a liquid solution of a nucleophilic agents: albumin or polyethylene glycol-Amine) and an electrophilic agent (i.e. PEG-Succinimidyl Glutarate) that is pre-mixed immediately prior to use or a biological liquid sealant (i.e., fibrinogen and thrombin). Electrophilic and/or nucleophilic group containing PEG or PEG (Thiol-CoSeal) components that are suitable for use as hemostats and/or sealants are well-known in the art. The liquid sealant can be applied before, during, or after insertion of the plug. The liquid sealant should be allowed to cross-link (for example, taking about 30 sec to 5 min) to form a seal within the lung tract and at the surface of the lung preventing air leaks.

The plug may be inserted into the lung tract using an applicator as known in the art. The applicator can be inserted into the tract and retracted as the plug is inserted. For example, the plug may be placed into the tract via a coaxial needle that is equal to or less than the diameter of a lung tract.

Optionally, the plug is inserted using pneumatic pressure until the plug is implanted in the desired location.

Optionally, the plug is held with a cylindrical mesh, moved into place, and the plug is deployed by expanding the mesh.

The following non-limiting examples further illustrate the invention.

Example 1

A series of tissue sealing plugs were made using SURGIFOAM® Absorbable Gelatin Sponges with (according to the invention) and without (comparative) polyethylene glycol (molecular weight: 300 Da and liquid at room temperature, with 88-96 cPs or mPas at 20 C). The plugs fabricated with PEGs were immersed in PEG, saturated, and then compressed into a cylindrical mold, squeezing out excess PEG. In order to fabricate the plugs without PEG, the SURGIFOAM® sponges had to be more aggressively compressed. 10 mL of PBS was slowly injected into the center of each plug using a needle. As the PBS was injected, the tip of the needle was pulled away along the length of the plug to ensure uniform hydration.

A volumetric swelling assay was performed on each plug as follows. The plug was placed into a 250 mL graduated cylinder with 30 mL ethanol. The final volume change was recorded. The variation in the results was within the resolution of the test method (±2 mL). Due to this consistency, no statistical analyses could be performed.

The average volumetric swelling of the plugs according to the invention containing PEG was 186%. In contrast, the average volumetric swelling of the comparative plugs not containing PEG was only 104%. In summary, the plugs according to the invention swelled an average of 81% more than the comparative plugs, and much more consistently. The inclusion of PEG300 in the plugs increased the extent and improved the consistency of swelling.

Example 2

Tissue sealing plugs according to the invention were evaluated for their ability to achieve pneumostasis in an ex vivo porcine lung model.

The plugs were made as follows. A SURGIFOAM® Absorbable Gelatin Sponge was manually compressed. The hydrophobic (smooth) side of the sponge was scored using a razor blade with 5 mm spacing between scores. 30 mL PEG300 was added to a container with a similar size as the SURGIFOAM® sponge. The hydrophobic side was placed down first and briefly allowed to absorb PEG300. The sponge was flipped and lightly compressed to absorb the majority of the remaining PEG 300. The sponge was manually rolled and placed into an ultra sized PLAYTEX® Gentle Glide tampon applicator as shown in FIG. 1. The prototype was placed in a nitrogen box until the ex-vivo assessment.

In this model, lung plucks were harvested fresh on the day of testing and kept moist until testing. Prior to testing, the lungs were placed on a ventilator to recruit collapsed alveoli (in order to open up collapsed airless alveoli). At the time of testing, lungs were connected to a RESPIRONICS respirator (commercially available from Phillips) to precisely control the pressure during ventilation cycles. The pressure was set to an inspiration pressure of 25 cm water and expiration pressure of 5 cm water (D 20 cm water).

Lung puncture defects were created with a lung tissue coring device having a diameter of 18 mm. The resulting puncture defects had a diameter of approximately 20 mm and a depth of approximately 3 cm. The air leak in the defect was assessed as severe with a bubble test. When plugs were applied, the pressure was reduced to inspiration pressure of 10 cm water and expiration pressure of 10 cm water (no change) to keep the lungs expanded.

Figure 2:
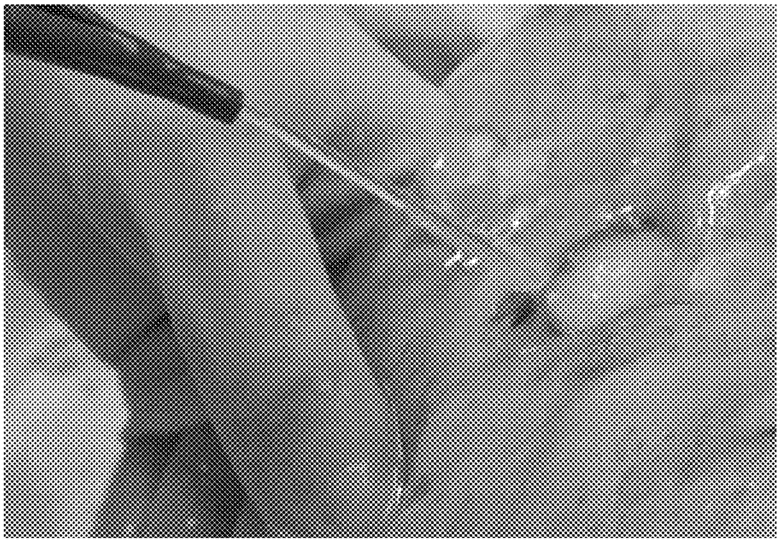
FIG. 2 is a photograph of the prototype of Example 2 after insertion.

FIG. 2 shows the prototype inserted into a defect. Surgifoam® plug and Evicel fibrin sealant. The liquid sealant was dripped into the defect then the rolled Surgifoam® plug was inserted, followed by additional fibrin sealant to cover the matrix and seal the tissue. No leaks were observed at 20 cm water. A small edge leak was observed when the pressure was increased to 35 cm water. The sealant adhered well to the surrounding tissue.

Example 3

Tissue sealing plugs according to the invention were tested with and without liquid PEG sealant in a porcine animal model as follows.

The liquid PEG sealant was made as follows. 5 mL 228 mg/mL PEG-Amine-5k, 50 mM carbonate (pH=8.6) was transferred to a 20 mL syringe. 5 mL 300 mg/mL PEG-SG-20k, 50 mM carbonate (pH=8.6) was transferred to a second 20 mL syringe. At the time of application, the two syringes containing the PEG solutions were connected with a dual syringe connector and passed varying number of times as described below. The syringe was connected to a SURGIFLO tip (commercially available from Ethicon) and completely expressed within 10 seconds.

The tissue sealing plugs were each made as follows. A SURGIFOAM® Absorbable Gelatin Sponge was manually compressed. The hydrophobic (smooth) side of the sponge was scored using a razor blade with 5 mm spacing between scores. 30 mL of PEG300, which was liquid, was added to a container with a similar size as the SURGIFOAM® sponge. The hydrophobic side was placed down first and briefly allowed to absorb PEG300. The sponge was flipped and lightly compressed to absorb the majority of the remaining PEG 300. Two sponges were manually rolled and placed into 20 mL syringe with the tip transected. The prototype was placed in a nitrogen box.

A coring device created a defect in an open setting. The lung plug that was removed was 2.5 cm in length when placed under negative pressure within a syringe. Minor bleeding was observed. A tissue sealing plug as described above was cut to a length of 2.5 cm to undersize the plug and to provide a place for the PEG sealant to pool. (The excess length was pushed out of the syringe and the plug was cut at the opening using a cutting blade.) The lung was held at a constant pressure of 10 cm $H_2O$. The plug was inserted into the bottom of the defect. 10 mL phosphate buffered saline was injected into the center of the plug via a 21-gauge needle. As the PBS was injected, the tip of the needle was pulled along the length of the plug to ensure uniform hydration. The plug swelled significantly and applied pressure to the walls of the defect.

The PEG liquid sealant was mixed using 6 passes and quickly applied. Bubbles were observed to be rising through the sealant, which was uncross-linked. Therefore, the ventilation of the lung was stopped (the ventilation tubing was removed from the respirator). Moderate air leak was observed via the bubble test at half ventilation. The surgeons believe the leak was originating from the rim of exposed lung tissue above the plug.

The PEG sealant was peeled away. A constant 10 cm $H_2O$ pressure was held for 1 minute to allow for cross-linking of new PEG sealant. The new sealant was prepared using 8 passes to accelerate crosslinking. The sealant was applied slowly and a change in viscosity could be felt by the surgeon during expression. A tendril formed at the tip of the syringe as the sealant was being applied. At half ventilation, no air leak was observed via the bubble test. At full ventilation, no air leak was observed. At 30 cm $H_2O$ (maximum pressure), no air leak was observed.

Example 4

In another test using the porcine animal model set forth in Example 3, a coring device created a defect of 2.5 cm in length. Moderate bleeding was observed. A 3 cm length plug made in accordance with Example 3 was inserted into the bottom of the defect with the intent to oversize the plug. 10 mL phosphate buffered saline was injected into the center of the plug via a 21-gauge needle. As the PBS was injected, the tip of the needle was pulled along the length of the plug to ensure uniform hydration. No leak was observed after 3 minutes at full ventilation; therefore, no sealant was applied.

Example 5

In another test using the porcine animal model set forth in Example 3, a coring device was used to create a 4 cm length tract. Very significant bleeding (the most observed on the day of testing) was observed. A plug made in accordance with Example 3 was inserted into the bottom of the defect and was oversized by approximately 5 mm in length. 10 mL phosphate buffered saline was injected into the center of the plug via a 21-gauge needle. As the PBS was injected, the tip of the needle was pulled along the length of the plug to ensure uniform hydration. No leak was observed after 3 minutes at full ventilation; therefore, no sealant was applied. The Surgeon stated the plug was "absolutely hemostatic and absolutely pneumostatic."

Example 6

The purpose of this study was to compare the swelling ability of compressed, rolled SURGIFOAM® plugs in PEG300, PEG600, and PEG1000. In some applications, swelling is an advantageous property that can help seal large leaks. The following materials were used:

SURGIFOAM® Absorbable Gelatin Sponge, Ethicon
PEG300, Sigma 20237
PEG600, Sigma 87333
PEG1000, Spectrum P0118
10× Phosphate Buffered Saline (PBS) pH=7.4

The SURGIFOAM® Absorbable Sponges were manually compressed. The hydrophobic (smooth) sides of the sponges were striated using a razor blade with 5 mm spacing between striations. The sponges were weighed to obtain an initial weight. 30 mL PEG was added to a container with a similar size as the SURGIFOAM® sponge. The hydrophobic side was placed down first and briefly allowed to absorb PEG. The sponge was flipped and lightly compressed to absorb the majority of the remaining PEG. Two sponges were manually rolled and placed into a 20 mL syringe with the tip transected. The plug was placed in a nitrogen box overnight. The plug was weighed again to obtain a final weight. The ends of the plug were transected for uniformity and the plugs were cut to 2 cm length.

The 2 cm plugs were weighed to obtain a dry weight. The plugs were placed in 100 mL 1×PBS and allowed to absorb for 10 minutes. The plugs were removed from PBS, shaken to remove loose water, and the mass was measured to obtain a wet weight. Swelling (%) was calculated gravimetrically.

PEG300 was a viscous liquid, PEG600 was a non-flowing paste, and PEG1000 was a solid at room temperature.

Both PEG 300 and PEG 600 resulted in a similar final composition including approximately 85% PEG as shown in the Table 1.

TABLE 1

| PEG Molecular Weight | Gelatin (g) | Total weight (g) | PEG (g) | PEG (% w/w) | Gelatin:PEG Ratio | Theoretical Gelatin:PEG Ratio (0% Porosity) |
|---|---|---|---|---|---|---|
| 300 | 2.433 | 17.763 | 15.329 | 86.302 | 6.3 | 6.8 |
| 300 | 2.500 | 19.409 | 16.909 | 87.119 | 6.8 | 6.8 |
| 300 | 2.484 | 18.860 | 16.375 | 86.828 | 6.6 | 6.8 |
| 600 | 2.714 | 17.870 | 15.156 | 84.812 | 5.6 | 6.8 |

Figure 3:
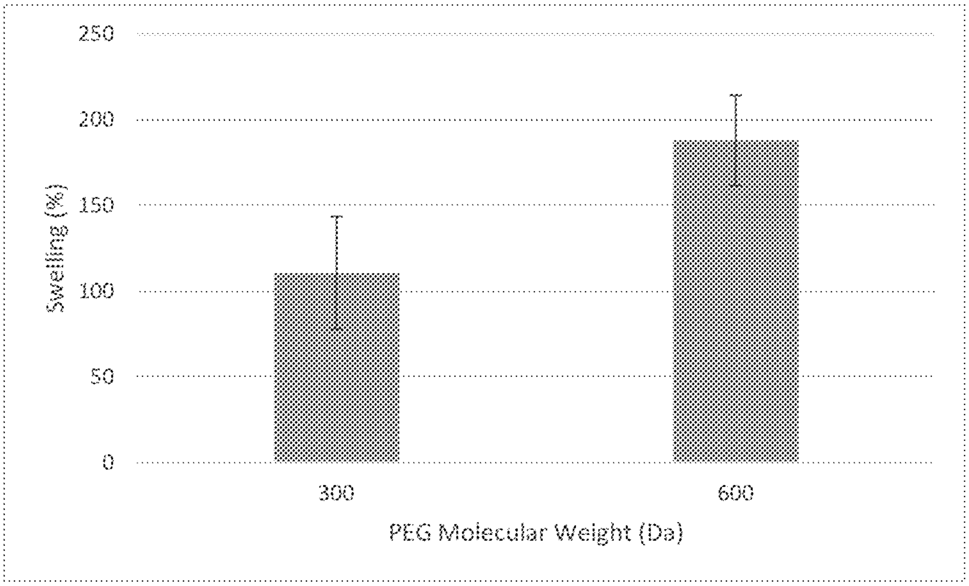
FIG. 3 is a graph of the PEG molecular weight (Da) versus swelling (%) for the results of Example 2.

Finally, the plug containing PEG600 resulted in a significantly greater degree of swelling (p=0.03), as shown in Table 2 and in FIG. 3.

TABLE 2 t-Test: Two-Sample Assuming Equal Variances

| | Variable 1 | Variable 2 |
|---|---|---|
| Mean | 110.6397 | 187.9736 |
| Variance | 1085.208 | 693.1254 |
| Observations | 3 | 3 |
| Pooled Variance | 889.1666 | |
| Hypothesized Mean Difference | 0 | |
| df | 4 | |
| t Stat | −3.17632 | |
| P(T <= t) one-tail | 0.016827 | |
| t Critical one-tail | 2.131847 | |
| P(T <= t) two-tail | 0.033654 | |
| t Critical two-tail | 2.776445 | |

We claim:

1. A tissue sealing plug comprising a compressed substrate comprising foamed gelatin having an interconnected pore structure impregnated with a polyethylene glycol that is liquid at room temperature, wherein 1) the weight ratio of polyethylene glycol to foamed gelatin in the substrate is about 4:1 to about 6.8:1,
2) the polyethylene glycol has a molecular weight of about 300 to about 450 Da according to gel permeation chromatography, and
3) the plug is substantially free of air.

2. The tissue sealing plug of claim 1, wherein the polyethylene glycol is substantially anhydrous.

3. The tissue sealing plug of claim 1 in the form of a cylinder.

4. The tissue sealing plug of claim 1 having a longitudinally tapered width.

5. The tissue sealing plug of claim 1 further comprising an additive selected from the group consisting of procoagulants, antifibrinolytics, would healing agents, contrast agents and combinations thereof.

6. The tissue sealing plug of claim 1, wherein the substrate comprises a surface feature selected from the group consisting of lines, ribs, barbs, grooves, notches, slits and combinations thereof.

7. The tissue sealing plug of claim 1, wherein the foamed gelatin is crosslinked, open cell foam.

8. A tissue sealing plug consisting of a cylindrical substrate comprising foamed gelatin impregnated with polyethylene glycol that is liquid at room temperature and has a molecular weight of about 300 to about 400 Da, wherein the weight ratio of polyethylene glycol to foamed gelatin in the substrate is about 4:1 to about 6.8:1 and the substrate is dry and substantially free of air.

* * * * *